United States Patent
Mahajan et al.

(10) Patent No.: US 11,197,616 B2
(45) Date of Patent: Dec. 14, 2021

(54) MULTISENSOR PHYSIOLOGICAL MONITORING SYSTEMS AND METHODS

(71) Applicant: THE REGENTS OF THE UNIVERSITY OF CALIFORNIA, Oakland, CA (US)

(72) Inventors: Aman Mahajan, Sherman Oaks, CA (US); William J. Kaiser, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 300 days.

(21) Appl. No.: 15/351,156

(22) Filed: Nov. 14, 2016

(65) Prior Publication Data
US 2017/0119255 A1 May 4, 2017

Related U.S. Application Data

(63) Continuation of application No. PCT/US2015/031021, filed on May 15, 2015.
(Continued)

(51) Int. Cl.
*A61B 5/0205* (2006.01)
*A61B 7/04* (2006.01)
(Continued)

(52) U.S. Cl.
CPC .......... *A61B 5/0205* (2013.01); *A61B 5/0051* (2013.01); *A61B 5/1135* (2013.01);
(Continued)

(58) Field of Classification Search
CPC .................. A61B 2562/0204; A61B 5/0205
See application file for complete search history.

(56) References Cited

U.S. PATENT DOCUMENTS

| | | | |
|---|---|---|---|
| 6,409,675 | B1 | 6/2002 | Turcott |
| 2003/0093003 | A1 | 5/2003 | Watrous |

(Continued)

FOREIGN PATENT DOCUMENTS

| | | |
|---|---|---|
| CN | 103153184 A | 6/2013 |
| JP | 2628690 B2 | 7/1997 |

(Continued)

OTHER PUBLICATIONS

Korean Intellectual Property Office (KIPO), International Search Report and Written Opinion, dated Aug. 21, 2015, related PCT International Application No. PCT/US2015/031021, pp. 1-14, with claims searched, pp. 15-22. The relevance of non-English language references WO 2014-035056 and JP 2628690 is indicated therein.

(Continued)

*Primary Examiner* — Puya Agahi
(74) *Attorney, Agent, or Firm* — O'Banion & Ritchey LLP; John P. O'Banion

(57) ABSTRACT

An integrated cardio-respiratory system that fuses continuously recorded data from multiple physiological sensor sources to acquire signals representative of acoustic events caused by physiological phenomena occurring in the cardiac and/or arterial structures underneath particular areas of the chest and/or neck to monitor cardiac and respiratory conditions.

14 Claims, 12 Drawing Sheets

Related U.S. Application Data

(60) Provisional application No. 61/993,876, filed on May 15, 2014.

(51) Int. Cl.
    *A61B 5/00*     (2006.01)
    *A61B 7/00*     (2006.01)
    *A61B 5/316*     (2021.01)
    *A61B 5/332*     (2021.01)
    *A61B 5/352*     (2021.01)
    *A61B 5/113*     (2006.01)
    *A61B 5/08*     (2006.01)
    *A61B 5/091*     (2006.01)

(52) U.S. Cl.
    CPC .............. *A61B 5/316* (2021.01); *A61B 5/332* (2021.01); *A61B 5/352* (2021.01); *A61B 5/6823* (2013.01); *A61B 5/6831* (2013.01); *A61B 5/7267* (2013.01); *A61B 7/00* (2013.01); *A61B 7/003* (2013.01); *A61B 7/04* (2013.01); *A61B 5/0803* (2013.01); *A61B 5/091* (2013.01); *A61B 2562/0204* (2013.01); *A61B 2562/04* (2013.01); *A61B 2562/06* (2013.01)

(56) References Cited

U.S. PATENT DOCUMENTS

| | | | |
|---|---|---|---|
| 2004/0167416 A1 | 8/2004 | Lee | |
| 2005/0074741 A1* | 4/2005 | Lee | A61B 5/0031 434/433 |
| 2007/0219480 A1* | 9/2007 | Kamen | G05D 7/0647 604/20 |
| 2007/0260285 A1* | 11/2007 | Libbus | A61N 1/36114 607/9 |
| 2008/0077026 A1 | 3/2008 | Banet | |
| 2008/0119750 A1* | 5/2008 | Patangay | A61B 7/04 600/528 |
| 2011/0060215 A1 | 3/2011 | Tupin, Jr. | |
| 2011/0213271 A1 | 9/2011 | Telfort | |
| 2011/0213274 A1* | 9/2011 | Telfort | A61B 7/003 600/586 |
| 2012/0041279 A1 | 2/2012 | Freeman | |
| 2012/0108915 A1* | 5/2012 | Corbucci | A61B 5/02028 600/301 |
| 2013/0116578 A1* | 5/2013 | An | A61B 5/0205 600/484 |
| 2013/0324804 A1* | 12/2013 | McKeown | A61B 5/0205 600/300 |
| 2013/0324868 A1* | 12/2013 | Kaib | A61N 1/3937 600/510 |
| 2014/0257122 A1* | 9/2014 | Ong | A61B 5/02405 600/515 |
| 2015/0126883 A1* | 5/2015 | An | A61B 5/02028 600/513 |

FOREIGN PATENT DOCUMENTS

| | | |
|---|---|---|
| WO | 2007-143535 A2 | 12/2007 |
| WO | 2011047207 A2 | 4/2011 |
| WO | 2012021900 A1 | 2/2012 |
| WO | 2014-035056 A1 | 3/2014 |

OTHER PUBLICATIONS

European Patent Office (EPO), extended European search report dated Dec. 12, 2017, related European patent application No. 15792464.8, pp. 1-9, claims searched, pp. 10-14.

IP Australia, Examination report No. 1 for standard patent application dated Feb. 15, 2019, related Australian patent application No. 2015249002, pp. 1-3, claims examined, pp. 4-11.

Japanese Patent Office (JPO), Office Action dated Jan. 15, 2019, related Japanese patent application No. 2016-564947, English-language translation pp. 1-3, Japanese-language office action pp. 4-7, claims examined pp. 8-15.

The State Intellectual Property Office of the People's Republic of China, The First Office Action dated Nov. 1, 2018, related Chinese patent application No. 201580024267.7, pp. 1-5, English-language translation, pp. 6-15, claims examined, pp. 16-23.

IP Australia, Examination report No. 2 for standard patent application dated May 7, 2019, related Australian patent application No. 2015249002, pp. 1-4, claims examined, pp. 5-11.

European Patent Office (EPO), examination report dated Aug. 28, 2020, related European patent application No. 15792464.8, pp. 1-7, claims examined, pp. 8-12.

European Patent Office (EPO), examination report dated Mar. 9, 2021, related European patent application No. 15792464.8, pp. 1-4, claims examined, pp. 5-8.

Intellectual Property India, official action dated Feb. 28, 2020, related India patent application No. 201617037537, pp. 1-6, claims examined, pp. 7-14.

The State Intellectual Property Office of the People's Republic of China, the Second Office Action dated Jul. 30, 2019, related Chinese patent application No. 201580024267.7, pp. 1-5, English-language translation, pp. 6-15, claims examined, pp. 16-22.

\* cited by examiner

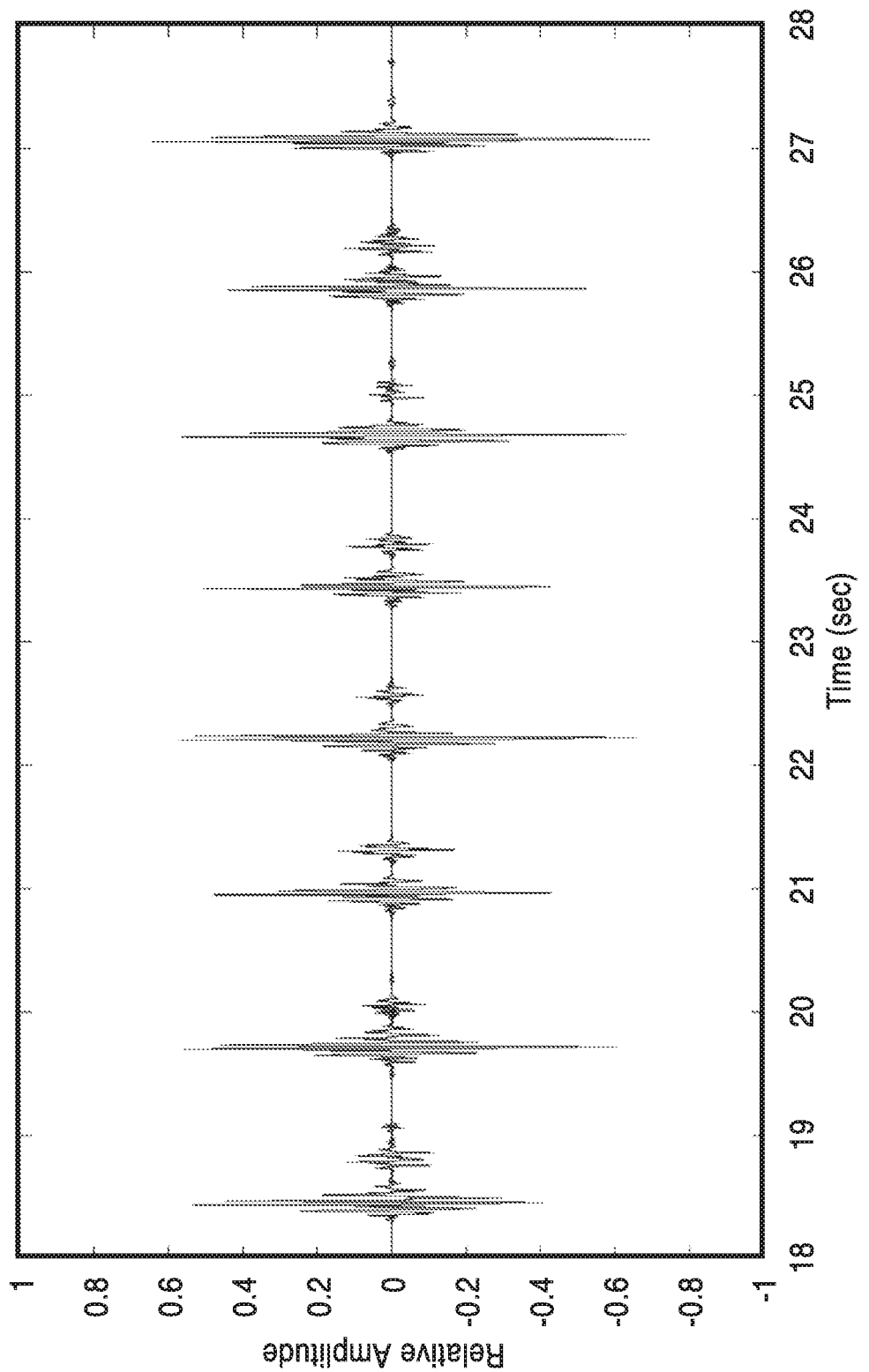

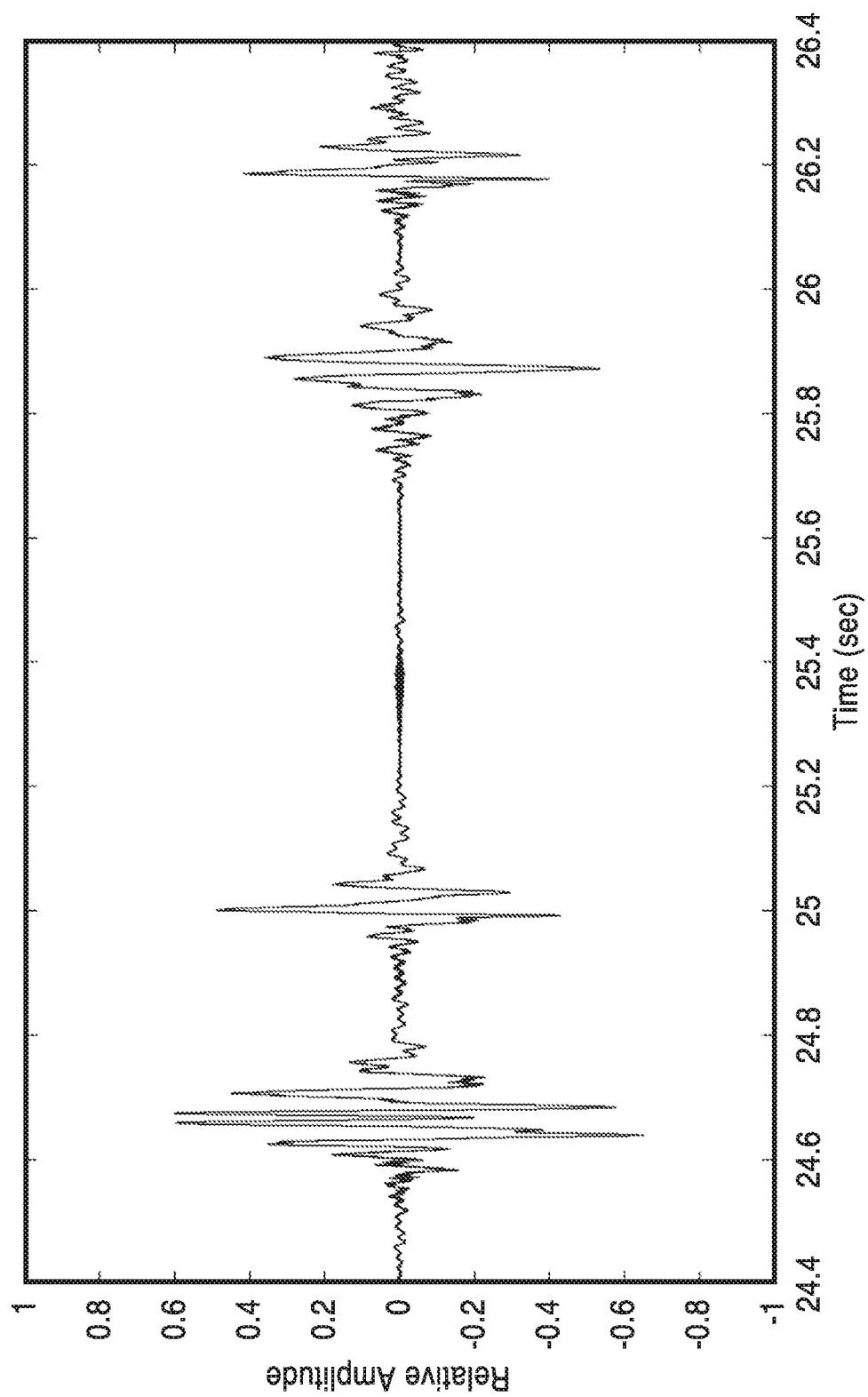

MULTISENSOR PHYSIOLOGICAL MONITORING SYSTEMS AND METHODS

CROSS-REFERENCE TO RELATED APPLICATIONS

This application is a 35 U.S.C. § 111(a) continuation of PCT international application number PCT/US2015/031021 filed on May 15, 2015, incorporated herein by reference in its entirety, which claims priority to, and the benefit of, U.S. provisional patent application Ser. No. 61/993,876 filed on May 15, 2014, incorporated herein by reference in its entirety. Priority is claimed to each of the foregoing applications.

The above-referenced PCT international application was published as PCT International Publication No. WO 2015/175904 on Nov. 19, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to cardio-respiratory diagnostic systems, and more particularly to multi-sensor cardio-respiratory diagnostic systems and methods.

2. Background Discussion

Acute worsening of cardiac and respiratory function is one of the most common causes for admission to hospital treatment and the leading contributor to healthcare delivery cost. Cardiac and respiratory complications also occur frequently during the post-operative period in patients who have undergone surgery. While clinical methods and technology solutions have been developed to mitigate the burden imposed, success for these past solutions has been very modest.

The limitations of past technology have been the inability to simultaneously acquire and analyze multiple, disparate sensor variables with continuous service and with real time analytics.

For example, the diagnosis of Congestive Heart Failure (CHF) ideally uses a combination of ECG, heart functional monitoring, respiratory system monitoring for detection of fluid in lungs and thoracic cavity, and motion and subject orientation. While these measurements may be obtained in sequence in the clinic at considerable operational cost, they are not available simultaneously and continuously.

BRIEF SUMMARY

The present description includes an apparatus having at least one acoustic sensor that is integrated into a carrier that can be worn by a human subject in the area of his or her abdomen. The one or more acoustic sensors may be connected to a computer processor either directly, or via a wired or wireless communications link. Software on the processor may function to acquire data from the acoustic sensor(s), compare data acquired from the acoustic sensor(s) with data in a conditional probability table, and determine one or more cardio or respiratory conditions of the subject based on said comparison. The conditional probability table may be populated or "trained" with data that is obtained empirically through studies of cardio-respiratory conditions. The software may be configured to detect waveform or other signatures in the time frequency domain that are characteristic of the cardio or respiratory conditions of the subject.

In one embodiment, each acoustic sensor may have a vibration source associated with the sensor. In one embodiment, the software may be configured to activate a vibration source associated with a sensor and then acquire signals from a different sensor to determine if the different sensor is detecting the vibration. Failure to detect vibration may indicate that the sensor is no longer coupled to the subject.

The wearable carrier may have various integrated sensors, including but not limited to a cardiac acoustic sensor, a respiratory acoustic sensor, an electrocardiogram (ECG) sensor, an electromyography (EMG) sensor, a thoracic motion sensor, a motion sensor, and an orientation sensor. These various sensors may be used to acquire and process cardio-respiratory data of the subject.

Another aspect is an integrated cardio-respiratory system that fuses continuously recorded data from multiple physiological sensor sources that monitor actual cardiac and respiratory motion as well as blood and air circulation. The system combines signal-processing algorithms with state-of-the-art high-speed imaging. Finally, the integrated cardio-respiratory system exploits design innovations and experience to produce a low cost, wearable, garment integrated solution that is comfortable and convenient for in-patients, outpatients, and well subject usage.

In one embodiment, an integrated cardio-respiratory system comprises a conveniently wearable structure compatible with garment integration, e.g. for adoption by apparel manufacturers. This exploits WHI fabric and conductive fabric systems for wearable sensing systems and relationships with large apparel manufacturers. This may include a low cost sensor and system integration with wireless technology and information technology including central enterprise computing for data delivery and subject guidance, wherein components and supporting services are composed of the lowest cost microelectronic and multiple data transport choices, and preferably low power electronics for biomedical devices. Further features include wireless recharge capability to permit convenient user support of energy recharge.

Another aspect is an integrated cardio-respiratory system having a sensor system including one or more of 1) electrocardiogram (ECG) signals by distributed sensors integrated into the system structure, 2) broadband acoustic signals obtained at high sensitivity while monitoring circulatory flow and events in the cardiac motion cycle by distributed sensors integrated into the system structure, 3) broadband acoustic signals obtained at high sensitivity monitoring of the esophagus through lung air flow and events in the breathing motion cycle by distributed sensors integrated into the system structure, 4) chest wall and thoracic volume monitoring using distributed displacement sensors integrated into the system structure, and 5) subject motion and orientation using motion sensors integrated into the system structure.

In another aspect, an integrated cardio-respiratory system includes one or more of: a combination of real-time imaging with acquisition of both electrophysiology signals and heart with broadband acoustic methods, and a combination of real-time measurement of thoracic motion and thoracic volume and lung mechanical response through broadband acoustic methods.

In one embodiment, the integrated cardio-respiratory system applies low amplitude, distributed acoustic signal sources to probe acoustic signal propagation to ensure both proper system physical orientation and characterization of coupling between internal organ acoustic sources and external sensing systems.

In another aspect, the system includes components associated with integrated signal sources in the sensor modules that permit measurement of the propagation of acoustic signal sources between sensor locations. This eliminates the uncertainty that would otherwise result due to variable coupling between sensors and subject tissue and variation in the propagation of acoustic signals within the subject. These integral acoustic emitters also enable detection of proper usage and usage assurance.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 8A and FIG. 8B are plots of an ICR acoustic sensor recorded at a location at the 4th rib 6 cm left of sternum (FIG. 8A) and an ICR acoustic sensor recorded at a location at the 4th rib 3 cm left of sternum (FIG. 8B).

FIG. 9A and FIG. 9B are plots of an ICR acoustic sensor at specified windows of the plots of FIG. 8A and FIG. 8B, respectively.

DETAILED DESCRIPTION

Figure 1:
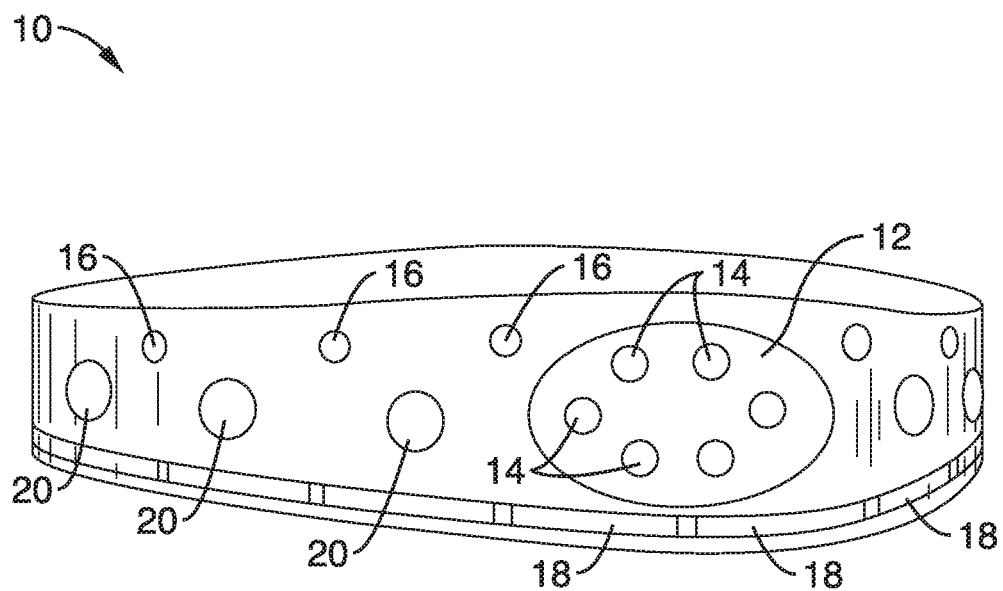
FIG. 1 is a schematic diagram of a multi-sensor integrated cardio-respiratory system in a belt-type configuration that can be worn at upper abdomen.

FIG. 1 shows a cross-sectional schematic diagram of a wearable multi-sensor integrated cardio-respiratory device 10 in a belt-type configuration that can be worn at upper abdomen. Device 10 may include an ECG array 12 of ECG elements 14 integrated with a plurality of acoustic transducer array elements 20. An array of displacement sensors 18 may also be included to measure displacement e.g. of the thoracic cavity. Additional sensors 16 may also be included to measure additional physiological characteristics (e.g. separate cardiac or respiratory acoustic sensors, EMG sensors, motion and orientation sensors, acoustic emitters).

Figure 2:
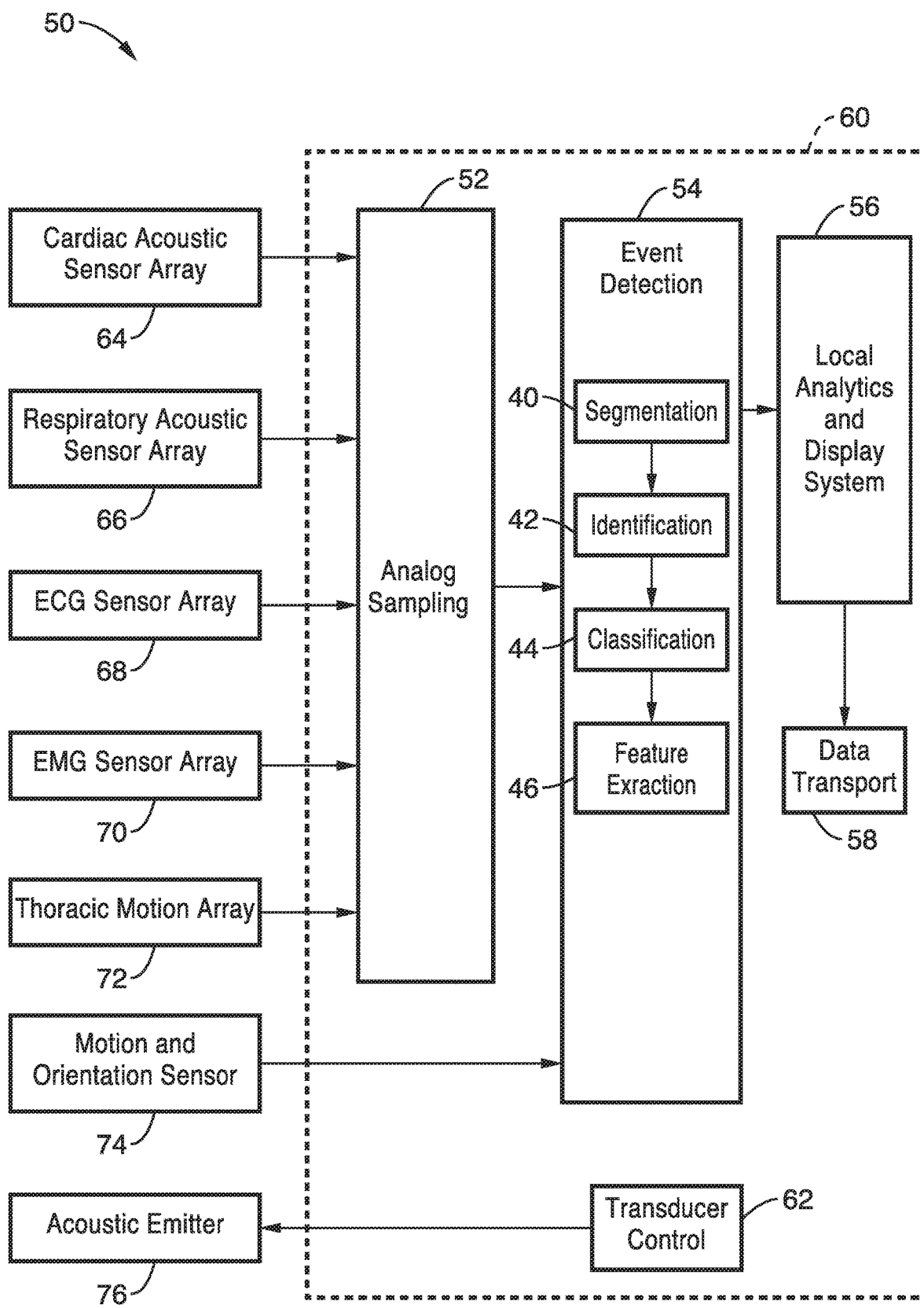
FIG. 2 is a system block diagram of an integrated cardio-respiratory system architecture with multiple sensors.

FIG. 2 shows a system diagram of an integrated cardio-respiratory system 50 architecture with multiple sensors. System 50 may be incorporated in a device such as external belt device 10, and includes application software 60 and at least one sensor, and preferably includes integration of two distinct sensors from among the group of sensors 64 through 76, e.g. cardiac acoustic sensor array 64, respiratory acoustic sensor array 66, ECG sensor array 68, EMG sensor array 70, thoracic motion array 72, motion and orientation sensors 74, and acoustic emitters 76. Output from sensors 64 through 72 is fed into an analog sampling module 52. Output from the analog sensing module 52 and motion and orientation sensors 74 is fed into an event detection module 54 for detection of physiological events, movement, etc. Output from acoustic emitter 76 is operated via transducer control unit 62. Data from the event detection module 54 may be further displayed via local analytics and display module 56, and may be further distributed via data transport module 58.

Sensors 64 through 76 are configured so that they may be located and repositioned as needed for clinical trial and in-field applications.

Figure 3:
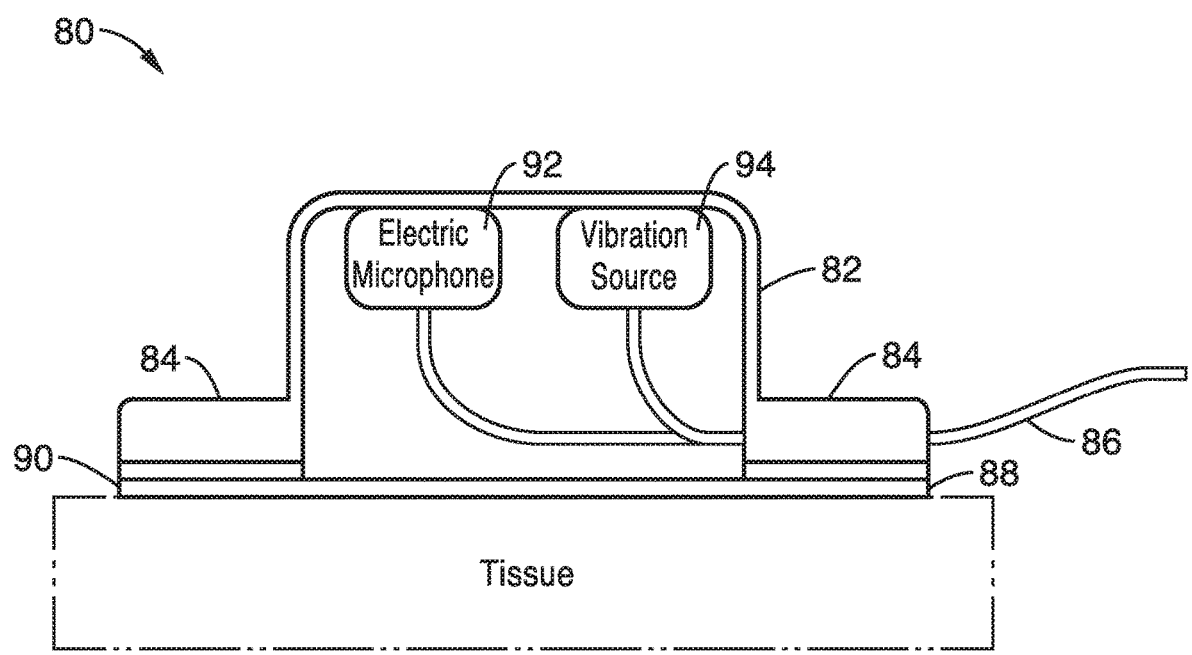
FIG. 3 shows a schematic diagram of an integrated cardio-respiratory system wearable acoustic sensor with optional vibration source.

FIG. 3 shows a schematic diagram of an integrated cardio-respiratory system wearable sensor 80 comprising an acoustic sensor (e.g. electric microphone 92), and optional vibration source 94 (e.g. acoustic emitter). The sensor 92 and vibration source 94 are disposed within housing 82 having a flange 84 for attachment to the patient via tegaderm sheet 90 and elastomer membrane 88 (which may be held together via adhesive (e.g. 3M Scotch-Weld MG100 Medical adhesive). Wearable sensor 80 is configured to periodically activate the vibration source 94 and determine if a different sensor 92 detects a vibration signal from the vibration source 94, both of which may be powered and operated via a cable 86.

Figure 4:
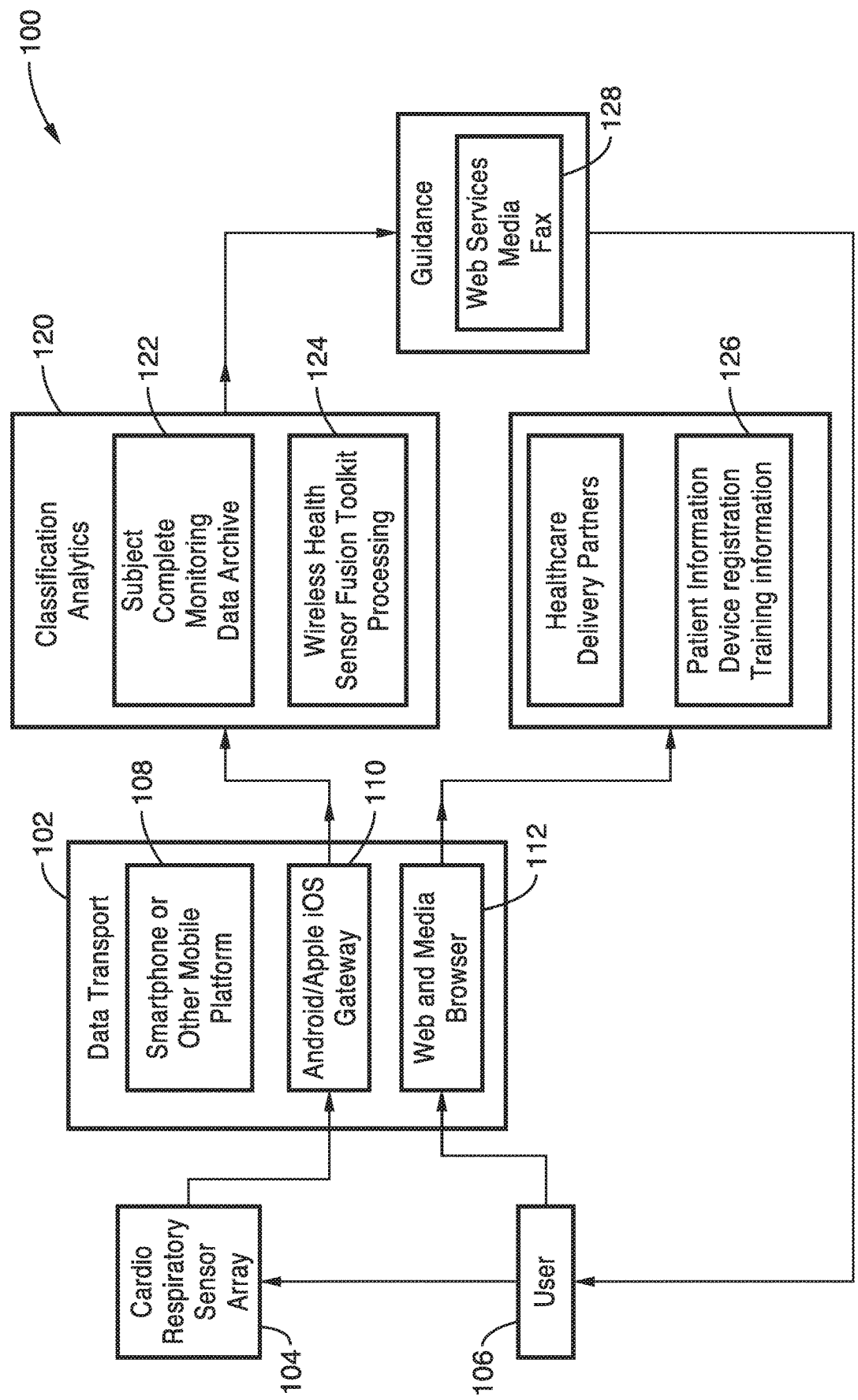
FIG. 4 shows a schematic diagram of an integrated cardio-respiratory system wearable data acquisition, transport, archive, analytics, and reporting architecture.

FIG. 4 shows a schematic diagram of an integrated cardio-respiratory system 100 configured for wearable data acquisition, transport, archive, analytics, and reporting architecture. Physiological data from the cardio-respiratory array 104 (which may include one or more sensors 64 through 76 shown in FIG. 2) of user 106 is received by a data transport device 102 (e.g. smart-phone 108 or other mobile platform via android/apple iOS gateway 110).

Data transport device 102 may also include web browser or media browser 112 for interaction with user 106 and healthcare delivery partners to distribute patient information, device registration, training information, etc. via interface module 126.

Via the android/apple iOS gateway 110 data transfer, the acquired sensor data is received by classification analytics module 120. Analytics module 120 includes a subject monitoring data archive 122 that is used with sensor fusion processing module 124 to process the data. Data archive may comprise a conditional probability table such that data acquired from the acoustic sensor may be compared with data in a conditional probability table to determine one or more cardio or respiratory conditions of the patient.

Additionally, a guidance module 128 may be provided including one or more of web services media or fax.

Unlike conventional acoustic methods that apply a single monitoring sensor with either manual inspection of data time series or analysis by computational methods, the application software modules 60 of FIG. 3 and 120 of FIG. 4 are configured for performing spatially-resolved multi-sensor signal processing on the data from the various sensors 64 through 76 (e.g. from the output of analog sampling module 52). The various spatial resolutions of sensors enables detection of waveform differences between monitoring locations. These monitoring locations each exhibit varying sensitivity to signal sources within both heart and lung.

Sensor locations are chosen to capture acoustic events caused by physiological phenomena occurring in the cardiac and/or arterial structures underneath particular areas of the chest and/or neck. In the case of heart monitoring, this includes detection of acoustic emission from each ventricle and valve. In one exemplary multi-sensor configuration for integrated cardio-respiratory (ICR), the four common clinical locations for auscultation are used. In this configuration, acoustic sensors are attached to the areas overlying the aortic valve, the pulmonary valve, the tricuspid valve, and the mitral valve. Alternately, a sensor can be placed at the carotid artery.

For ICR multi-sensor signal processing, at least one electrocardiogram (ECG) signal and signals from acoustic sensors are recorded synchronously. All sensors are integrated into the system structure. The system is capable of acquiring acoustic signals from a single sensor, or from multiple sensors. The distribution of sensors in multi-sensor mode allows for acquisition of spatial and temporal information regarding acoustic event source and propagation. Also, as will be described, the multi-sensor mode allows for novel system fusion algorithms that enhance system robustness.

For ICR multi-sensor signal processing, event detection module 54 is configured to operate on the combined records of one or more ECG sensors 68 and each acoustic ICR sensor 64, 66 to derive sources of evidence by time and frequency domain signal processing. Sources of evidence may include: 1) identification of time of occurrence, amplitude, and frequency-domain characteristics of each segment of the acoustic emission waveform relative to each heartbeat (for heart monitoring from sensors 64) or breath (for respiratory system monitoring from respiratory sensors 66); 2) identification of time of occurrence, amplitude, and frequency-domain characteristics of each segment of the acoustic emission waveform for each sensor with detection of differences in each characteristic between all sensor sources, including ECG sensors 68; 3) identification of time of occurrence of subject behavior and behavior time history for determination of influence of motion and exertion on subject state.

Figure 5A:
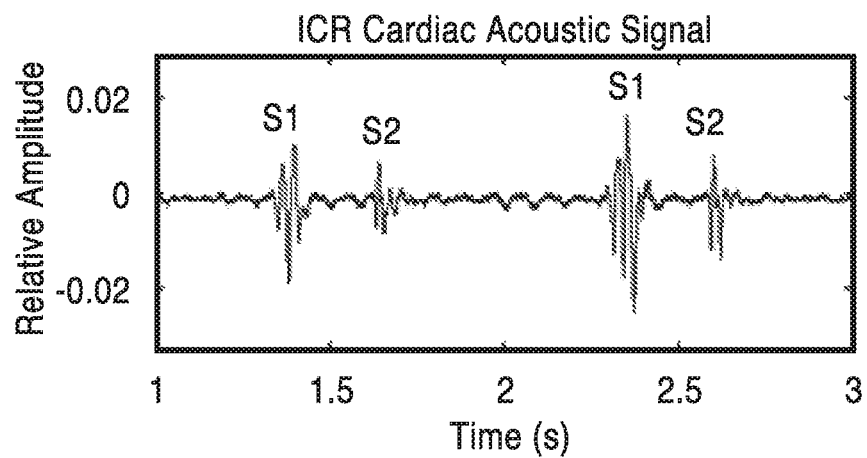
FIG. 5A is a plot of an exemplary ICR cardiac acoustic signal with synchronized ECG, showing heart sound events S1 and S2.
Figure 5B:
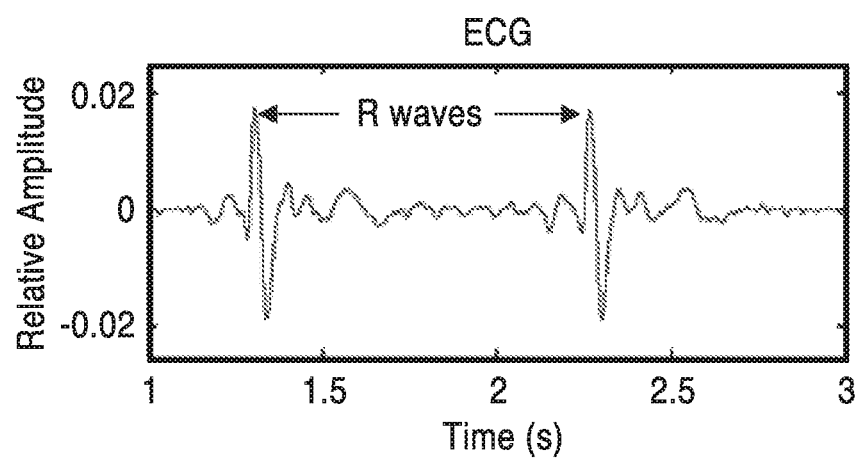
FIG. 5B is a plot of an exemplary ICR cardiac acoustic signal with identified R waves.

In a preferred embodiment, event detection module 54 includes a segmentation routine 40 in which the ECG signal (from ECG sensor 68) is used to decompose, or segment, each acoustic signal into frames, in which each frame corresponds to the time interval associated with one cardiac cycle. FIG. 5A shows a plot of an exemplary ICR cardiac acoustic signal with synchronized ECG, showing heart sound events S1 and S2. This is achieved by the identification of an ECG signature occurring within each heartbeat, namely the R-wave peak (shown in FIG. 5B). The frames are segmented so that a frame begins 0.1 s before one R-wave peak, and ends 0.1 s before the next R-wave peak. This segmentation has been shown to be effective in capturing the acoustic events of a cardiac cycle and acquisition of spatial and temporal information regarding acoustic event source and propagation.

Figure 6A:
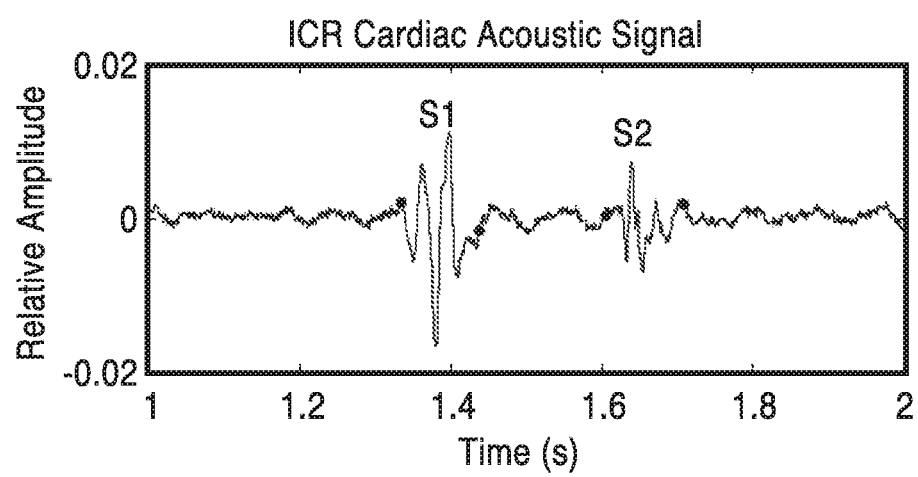
FIG. 6A is a plot of an exemplary ICR cardiac acoustic signal.
Figure 6B:
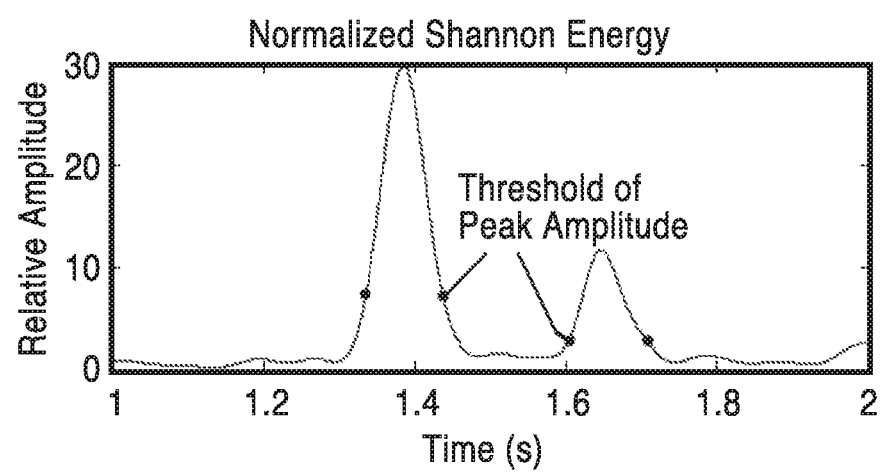
FIG. 6B is a plot of normalized Shannon energy signal envelope.

The segmented data is then processed by an acoustic event identification routine 42. In order to identify acoustic events, each frame of the raw acoustic signal is first processed to yield a smooth envelope. This is achieved via a low-pass filtered, normalized Shannon Energy transformation. Peaks of this envelope are identified as event candidates. Start and end points are designated as the times at which the envelope signal rises above an amplitude threshold and returns to a level below amplitude threshold, respectively (see FIG. 6A and FIG. 6B). This threshold is referred to as the Threshold of Peak Amplitude.

Event Duration is then calculated using the start and end points, and can be used to remove false events. Minimum Event Duration is the minimum time duration required of an event candidate for it to be considered a cardiac event. Events of shorter duration are declared as noise events. Maximum Event Duration is the maximum time duration allowed of an event candidate for it to be considered a cardiac event. Events of longer duration are declared as noise events.

Once acoustic events have been identified, they can be classified with classification module 44 as one of many clinically relevant heart sound types, namely S1, S2, S3, S4, or murmur. The event duration and time from the start of the cardiac cycle to the onset of the acoustic event are used for event classification; the acoustic event is designated as the heart sound type most likely to occur with this duration at this point in the cardiac cycle. This probability was determined a priori by examining several records of acoustic signals from healthy and afflicted subjects.

In one embodiment, the state of a subject's heart and lung function can be inferred through an ICR State Classifier that includes a Bayesian classifier. The classifier system operates on the sources of evidence determined by ICR spatially-resolved multi-sensor signal processing to infer the subject state. The classifier system itself relies on prior determination of the conditional probability relating observed sources of evidence to subject state. This conditional probability is computed based on system training operations. System training includes:

1) Measurement of all ICR signal sources for a range of subject conditions with subjects exhibiting the characteristics of each state corresponding to healthy or each disease condition, varying age, gender, physiological characteristics, fitness measures, and activity history prior to the time of measurement and activity at the time of measurement.

2) Measurement of all ICR signal sources as above while simultaneously acquiring real time imaging via 3-D and 4-D ultrasound as well as MRI and also with respiratory system flow and gas composition monitoring.

After system training is complete based on the evidence above, the ICR state classifier now operates on ICR data sets to provide both subject state classification as well as a measure of the certainty associated with the classification.

Finally, acoustic event feature extraction is performed via module 46. Several time and frequency domain features of the acoustic events for each heartbeat are evaluated and stored for analysis: 1) Event Duration and Time From Start of Cardiac Cycle, as described above; 2) Peak Amplitude of Signal, which is the amplitude of the peak of greatest magnitude during the time interval of the acoustic event; 3) Average Amplitude of Signal, which is the average amplitude of the peaks during the time interval of the acoustic event; 4) Maximum Amplitude of Envelope Signal, which is the maximum value of the envelope of the signal during the time interval of the acoustic event; 5) Zero-Crossing Rate, which is the rate at which the signal changes sign during the time interval of the acoustic event; 6) Maximum Value of Specified Frequency Band Energy, which is the maximum value of the energy in specified frequency bands during the time interval of the acoustic event; and 7) Compression Time to Ejection Time Ratio; which is the ratio of time during which the heart is in the compression phase of the cardiac cycle to the time during which it is in the ejection phase of the cardiac cycle. The compression phase is estimated as the duration of the S1 event. The ejection phase is estimated as the time from the end of the S1 event to the start of the S2 event.

In one embodiment, the ICR acoustic event features extracted from module 46 described above can be used as the input to a regression model, in which the output is a desired physiological measurement to be predicted. Such a regression model will have been previously trained on data from separate data sources for which both ICR acoustic event features and ground truth values of the desired physiological measurement have been obtained. This regression model can be a neural network regression model, a linear regression model, or a fusion of the two.

A linear regression model assumes a linear relationship between input and desired output, and trains coefficients to map input to output in a linear fashion. A neural network regression model also performs a mapping from input to output; however it does not assume a linear relationship, and thus can account for nonlinear relationships between input and output. Because the mapping algorithms in linear regression and neural network regression are different in nature, a fusion of the two models, in which the respective weights are optimized in the training stage, can achieve improved predictive performance of physiological measurement based on ICR acoustic event features.

As opposed to a regression model, in which the output is a continuous value, a classification model can map input to a particular group or class out of many potential classes. A Bayesian classifier is a statistical tool in which a model is built based on the statistics of the input feature set, in this case being the set of ICR acoustic event features. The classes for the ICR Cardiac Acoustic Classifier can be various pathological cardiac conditions as well as a healthy/normal class. Like the regression model described earlier, this model is previously trained on data from separate data sources, from which the ICR acoustic event features are known, as are the associated cardiac conditions.

In a multi-sensor system, situations in which the integrity of one or more sensor signals is compromised pose a significant challenge to signal processing. When using acoustic sensors, several of these types of situations may arise. This may be due to external noise, such as tapping of the sensor or rubbing against the sensor. It can also be caused by poor attachment or temporary disconnection of the sensor. Thus, an individual sensor may fail in unpredictable fashion.

It is therefore beneficial to develop a robust system that maximizes the amount of information that can be extracted from sensors when the signals are intact, while also discarding signal segments that are lost or corrupted by noise.

Analytical models are trained on previously obtained data, for each possible combination of sensors. Thus, if there are four sensors being utilized, there will be 15 such models (see Table 1). This represents all possible scenarios in which the signal integrity from one or more, but not all, sensors is compromised. The models can be either regression models or classification models, depending on the desired output. Possible sensor combinations for multi-sensor fusion and the corresponding analytical models. A "+" sign indicates the signal from a particular sensor is intact, a "−" sign indicates the signal is noisy or has been lost.

When a new data stream from acoustic sensors is acquired, it is analyzed on a frame-by-frame basis, in which each frame corresponds to a heartbeat. For each sensor, a determination is made regarding the quality of the signal in that frame. If an acoustic event is identified in the frame, the sensor is determined to be intact for that frame, and it will be utilized. If no acoustic event is identified, the information from that sensor for that particular frame is discarded. Next, the algorithm will determine the current combination of intact sensors for the frame, and will select the corresponding analytical model to use.

In this manner, the acoustic signal from a given sensor will be used for analysis whenever it is determined to possess a high quality signal, and it will be discarded when this is not the case. The sensor fusion system then intelligently combines data from all high quality signals. This greatly enhances the robustness of the system.

EXAMPLE

Two tests were performed using the ICR system on a healthy subject. FIG. 7 through FIG. 10 include data associated with time synchronized measurements of ICR acoustic and ICR dry electrode ECG (based on Plessey EPIC sensors).

Figure 7:
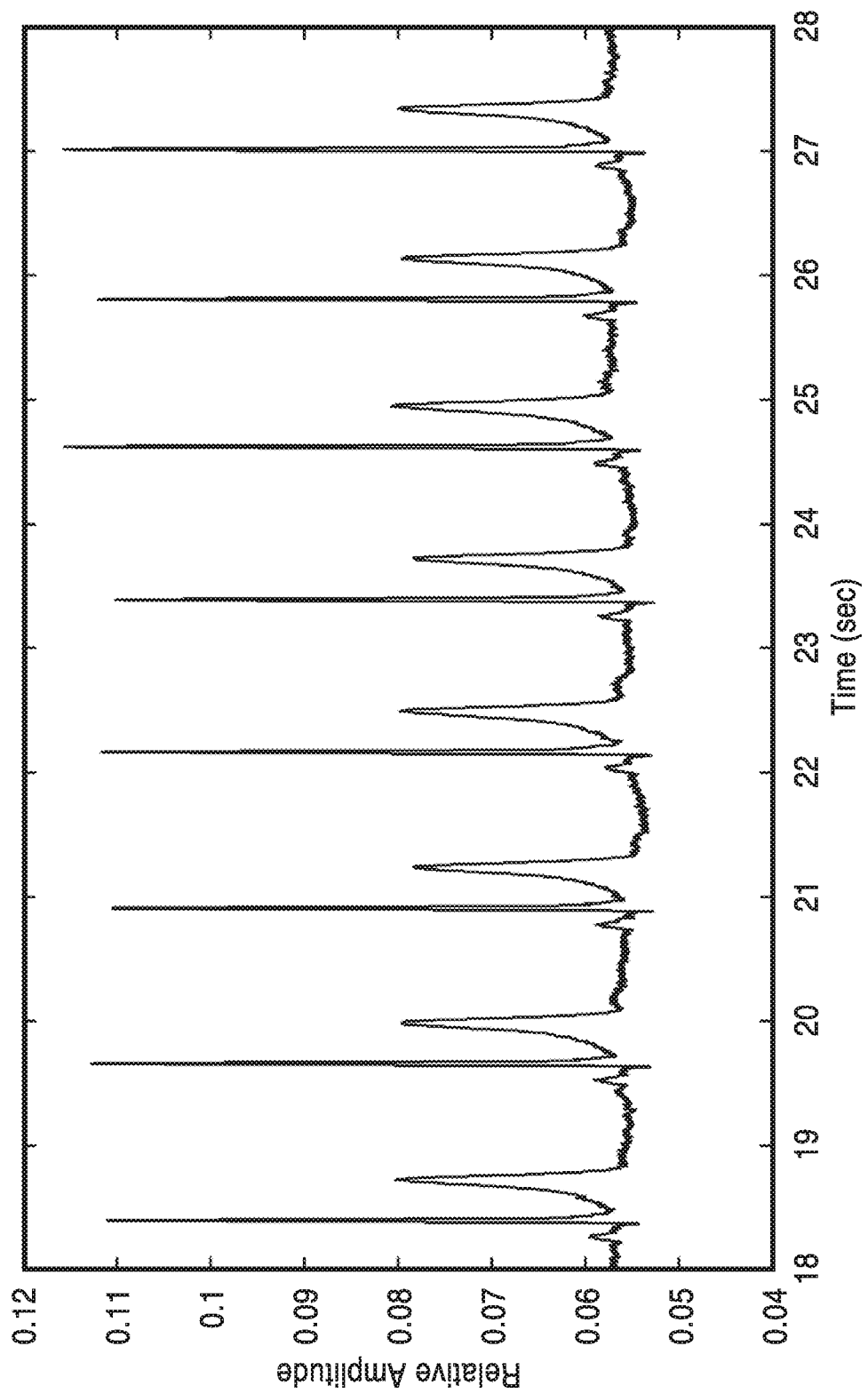
FIG. 7 is a plot of an ECG record at a location at the $3^{rd}$ rib 3 cm left of sternum and right midaxillary.
Figure 8B:
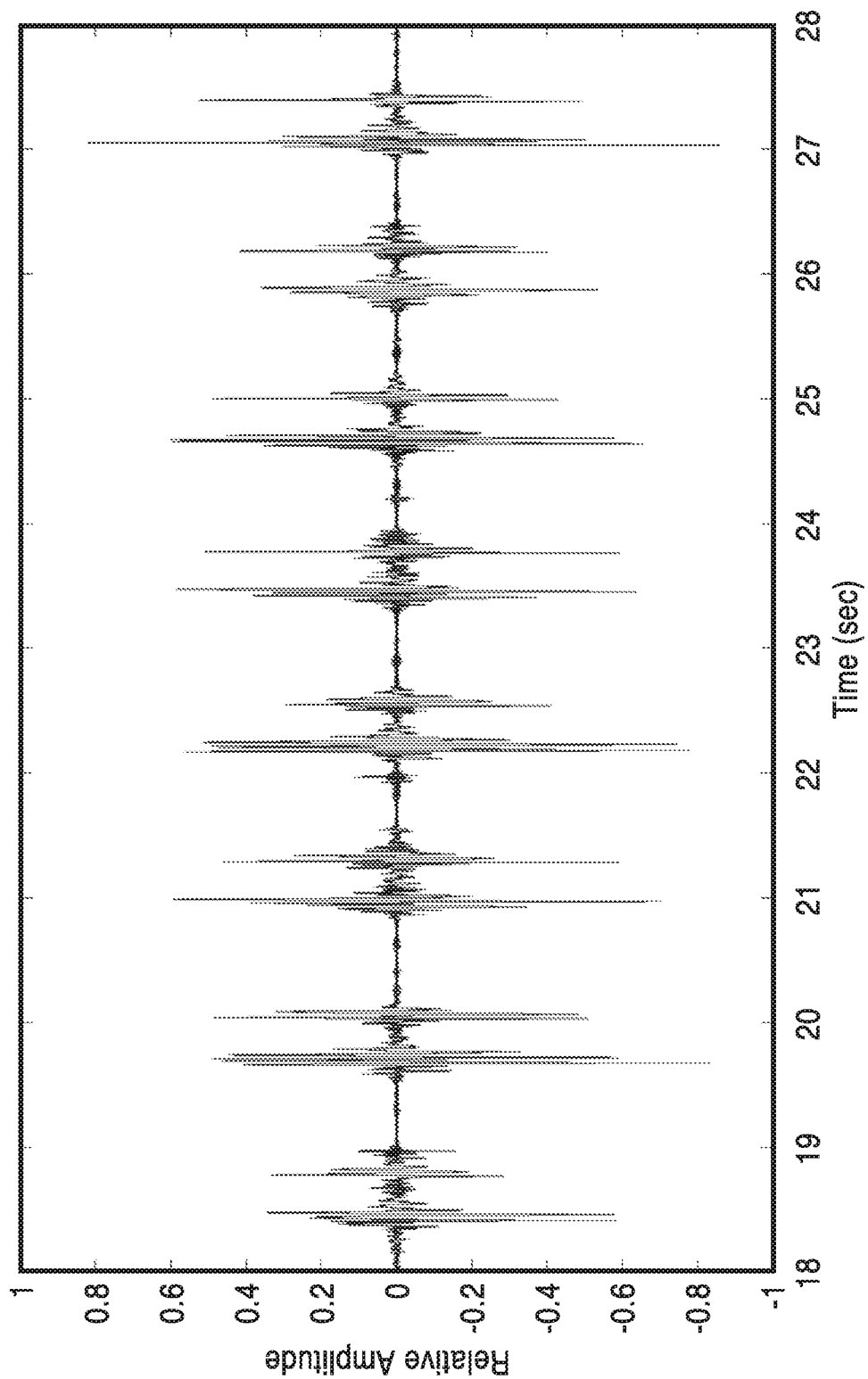
Figure 9A:
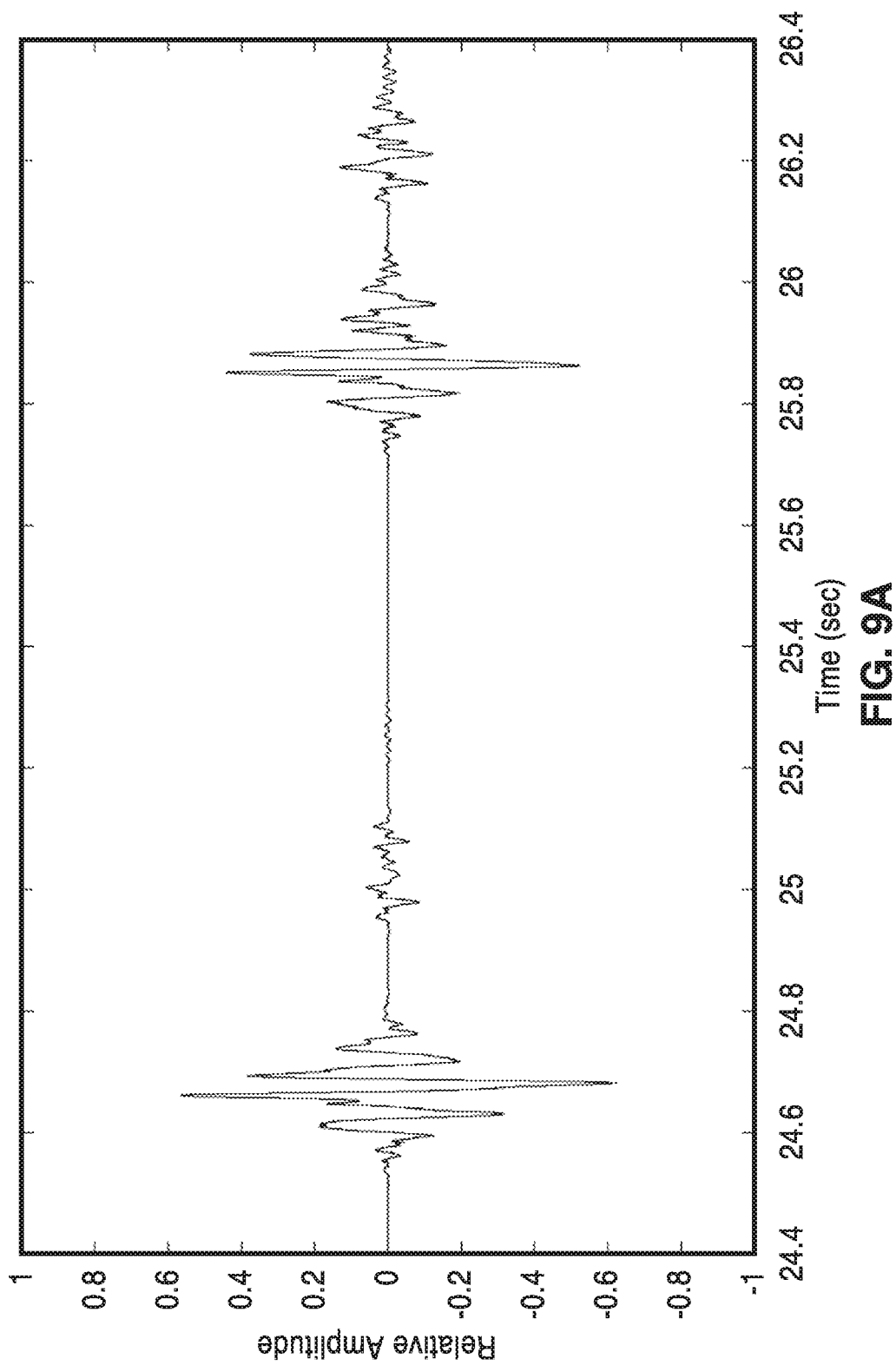
Figure 10:
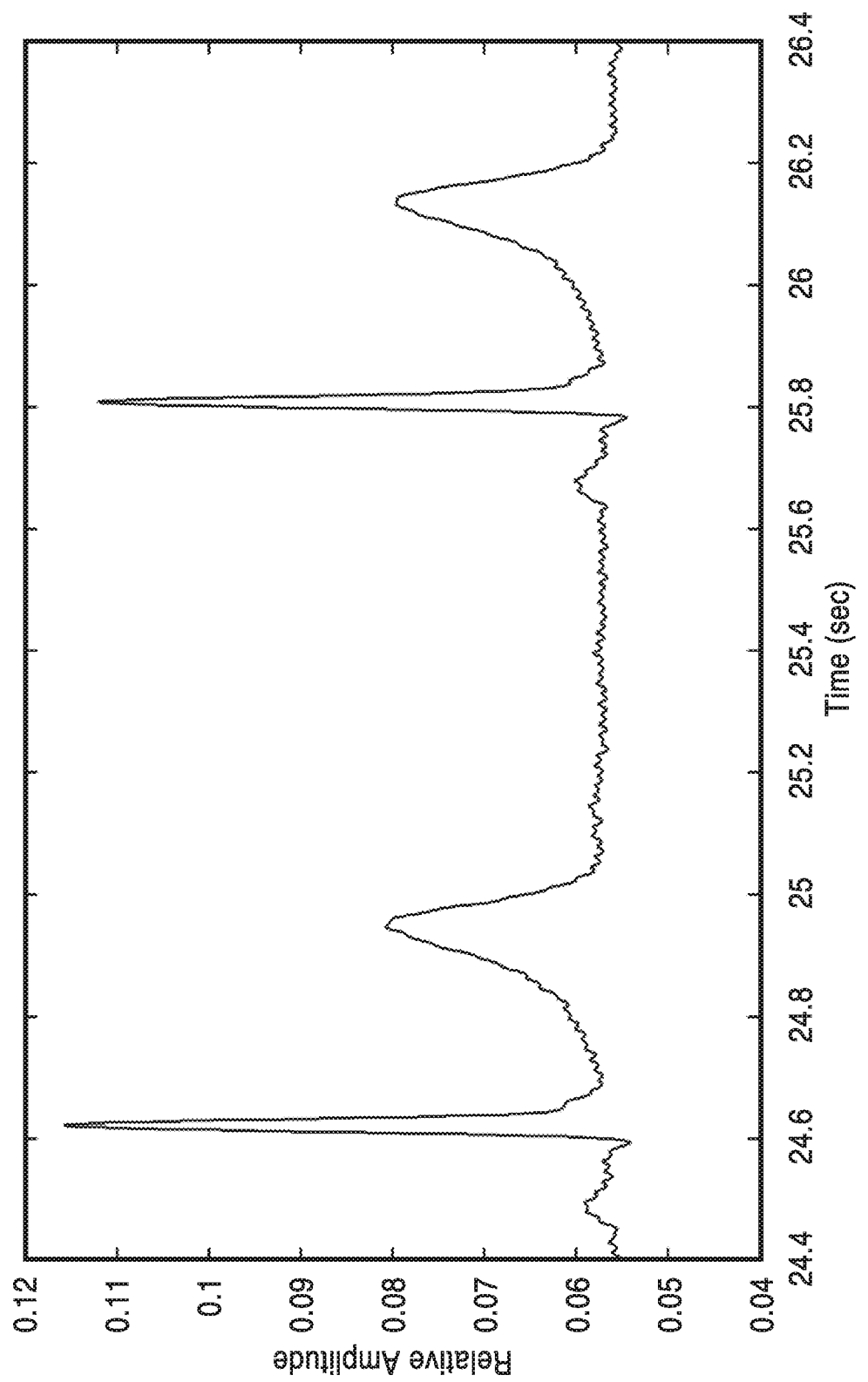
FIG. 10 is a plot of an ECG record for a specified window of the plot of FIG. 7.

ICR acoustic sensors were placed at 3 cm left of sternum center at the 4th rib (approximately above left ventricle) and at 6 cm left of sternum at the 4th rib (left of the left ventricle region). ECG sensors were placed at 3 cm left of sternum center at 3rd rib and also at right midaxillary (providing a potential reference). FIG. 7 shows a plot of an ECG record at a location at the 3rd rib 3 cm left of sternum and right midaxillary. FIG. 8A and FIG. 8B are plots of an ICR acoustic sensor recorded at a location at the 4th rib 6 cm left of sternum (FIG. 8A) and an ICR acoustic sensor recorded at a location at the 4th rib 3 cm left of sternum (FIG. 8B). FIG. 9A and FIG. 9B are plots of an ICR acoustic sensor at specified windows of the plots of FIG. 8A and FIG. 8B, respectively. FIG. 10 is a plot of an ECG record for a specified window of the pot of FIG. 7.

The ICR experimental results have established such that spatial resolution of ICR sensors enables detection of waveform differences between monitoring locations. These monitoring locations each exhibit varying sensitivity to signal sources within both heart and lung. In the case of heart monitoring, this includes detection of acoustic emission from each ventricle and valve.

The ICR multi-sensor signal processing system and methods detailed above have cardiac monitoring ability to assess rate, rhythm, and early recognition of patterns of cardiac activity that, in conjunction with respiratory monitoring, provides vastly superior diagnostic information.

The system and methods detailed above have the further ability to assess mechanical function by precisely measuring myocardial motion and orientation of different left and right ventricular wall segments to allow early detection of systolic and/or diastolic dysfunction (e.g. myocardial ischemia and infarction) in cardiovascular diseases. With respect to the native valve and prosthetic valve, the system is capable of interrogating the structure and function of the valves to allow early diagnosis of valve disease. Further monitoring capabilities include assessment of stroke volume and ejection fraction of right and left ventricle for remote monitoring of cardiac function and worsening of heart failure. The system of the present disclosure enables monitoring of mechanical function (e.g. organ motion) through use of broadband acoustic sensing.

The system and methods detailed above have the further ability to incorporate data sources from sensors located at the neck where signals from carotid artery blood flow and blood pressure changes are detected. This capability permits the measurement of transit times of blood flow between the cardiac valve and the carotid artery measurement site. This data is also combined with the additional sensor data detailed above to refine yet further the accuracy of cardiac function measurement.

The system and methods detailed above may also assess pressures and blood flow in cardiac chambers for management of heart failure, pulmonary hypertension, assessment of hypovolemia, etc. Chest wall and diaphragmatic movement may also be assessed, along with selective assessment muscular effort and pattern of chest wall vs. diaphragmatic motion in conjunction with cardio-respiratory indicators for further enhancement of diagnostic capabilities.

The system is configured to assess respiratory rate and patterns of breathing, and allow for recognition of patterns of breathing that serve as early indicators of respiratory compromise, along with Integrated and distributed thoracic volume and synchronization of volume change. The system may include one or more of: acoustic monitoring arrays, localization, dry contact EMG, etc. The system may also include thoracic and diaphragmatic expansion sensors located at upper and lower abdomen, respectively. These sensors may be based on measurement of strain or other variables beneficial for detection of such expansion through measurement of changes in girth or displacement of the upper and lower abdomen. The data from these sensors that include one, two, or more expansion measurement systems may be combined to determine relative changes associated with thoracic and diaphragmatic breathing profile for determination of pulmonary condition.

The system is further configured (e.g. with acoustic signal processing with distributed sensors) to detect the presence and amount of water/fluid in the lungs, e.g. via global and regional assessment of excess fluid in and around lungs will aid in better differential diagnosis of heart failure, pleural effusions, and pulmonary hypertension. Further capabilities include detection of regional changes in lung parenchyma allowing diagnosis of pneumonia, other consolidations, lung fibrosis, and rejection in transplants. Non-invasive pressure and flow of blood in pulmonary blood vessels can be quantified to greatly enhance diagnostic and therapeutic abilities. Patterns of airflow in both large and small airways in disease can also be assessed to allow monitoring and diagnosis of conditions such as emphysema, COPD, Asthma, or any other obstructive or restrictive disease. This may be achieved through detection of air flow patterns through time profile of distributed sensor measurements.

Signal processing, sensor fusion, and event classification have been applied for analysis of cardiac and respiratory state. State classifiers generally require system training for optimization of classifier discrimination. Traditional methods are limited by lack of ground truth. The Integrated cardio-respiratory system of the present description applies a novel approach that exploits detailed subject state by methods including high speed and high resolution imaging, with time-synchronized multi-sensor measurements. This combination enables the training of event and state classifiers.

Subject physiological characteristics and sensor system application variability reduce classifier performance in conventional systems. The integrated cardio-respiratory system of the present description incorporates an in-situ calibration method that permits normalization of measurements to variations in both subject physiological characteristics (including body composition) and the mechanical characteristics of a wearable sensor array and its coupling to the subject.

Electrocardiogram (ECG) and electromyography (EMG) signals provide a measurement of organ function drive. However, organ response revealing the presence of disease conditions is not determined by these methods. The integrated cardio-respiratory system of the present disclosure includes multi-sensor synchronization of ECG and EMG accordingly with synchronized measurement of organ motion via an acoustic sensor system.

The variability in subjects and physiological conditions introduces uncertainty for conventional single point measurements. The integrated cardio-respiratory system of the present disclosure includes distributed sensing for, ECG, cardiac acoustic internal motion sensing, respiratory acoustic internal motion and fluid sensing, as well as thoracic expansion detection. In addition, conventional remote diagnostic methods are limited by the inherent variability in physiological state resulting from variations in subject state (subject orientation, subject motion, behavior, states of wakefulness, states of sleep, and others). The integrated cardio-respiratory system of the present disclosure resolves this uncertainty by integrating motion sensing systems into the continuously wearable solution to allow for subject state and behavior sensing.

In addition, the integrated cardio-respiratory system of the present disclosure includes sensors that may be located and repositioned as needed for clinical trial and in-field applications.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A multi-sensor cardio-respiratory system, comprising: (a) a first sensor comprising an acoustic sensor disposed at a location external to a subject; (b) a second sensor disposed at a location external to a user, the second sensor configured to measure a physiological characteristic of the subject; (c) a computer processor; and (d) a memory storing instructions executable on the processor, the instructions, when executed by the processor, performing steps comprising: (i) synchronously acquiring data from the first sensor and the second sensor; (ii) detecting one or more events in an acoustic signal acquired from the first sensor as a function of acquired data from the second sensor; and (iii) determining one or more cardio or respiratory conditions of the patient based on the one or more detected events.

2. The system of any preceding embodiment: wherein the first sensor is located at a different location on the subject than the second sensor; and wherein various spatial resolution of sensors enables detection of waveform differences between the different locations.

3. A system in any of the previous embodiments, wherein detecting one or more events comprises acquiring spatial and temporal information regarding acoustic event source and propagation.

4. A system in any of the previous embodiments, wherein the second sensor comprises an electrocardiogram (ECG) for monitoring an ECG signal of the patient.

5. The system of any preceding embodiment: wherein the first sensor comprises a cardiac acoustic sensor located at a location external to the subject associated with the subject's heart; and wherein the system further comprises a third sensor comprising a respiratory acoustic sensor located at a location associated with the subject's lung.

6. The system of any preceding embodiment, further comprising a third sensor configured for real-time measurement of one or more of thoracic motion and thoracic volume and lung mechanical response.

7. The system of any preceding embodiment: wherein the acoustic sensor is one of an array of acoustic sensors integrated into the wearable sensor unit; each said acoustic sensor having an associated vibration source integrated into the wearable sensor unit; said instructions when executed by the processor performing steps comprising periodically activating the vibration source associated with a sensor and determine if a different sensor detects a vibration signal from the vibration source.

8. A system in any of the previous embodiments: wherein detecting one or more events comprises segmenting an acoustic signal of the acoustic sensor into frames; and wherein each frame corresponds to a time interval associated with one cardiac cycle.

9. The system of any preceding embodiment, wherein the frames are segmented so that each frame begins and ends relative to successive R-wave peaks.

10. The system of any preceding embodiment, wherein when executed by the processor the instructions further perform steps comprising identifying peaks in the acoustic signal as event candidates.

11. The system of any preceding embodiment, wherein when executed by the processor the instructions further perform steps comprising classifying event candidates as one of a plurality of heart sound types.

12. The system of any preceding embodiment, wherein when executed by the processor the instructions further perform steps comprising extracting acoustic event features as a function of time and frequency domain features of acoustic events for each heartbeat.

13. The system of any preceding embodiment, wherein when executed by the processor the instructions further perform steps comprising inputting the extracted acoustic event features into a regression model to output a desired physiological measurement to be predicted.

14. The system of any preceding embodiment, wherein when executed by the processor the instructions further perform steps comprising inputting the extracted acoustic event features into a plurality of classification model models trained on previously obtained data; and wherein each model represents all possible scenarios in which the signal integrity from one or more, but not all, sensors is compromised.

15. A method for performing cardio-respiratory monitoring, comprising: synchronously acquiring acoustic data from a first sensor and electrocardiogram (ECG) data from a second sensor; detecting one or more events in an acoustic signal acquired from the first sensor as a function of acquired ECG data from the second sensor; and determining one or more cardio or respiratory conditions of the patient based on the one or more detected events.

16. The method of any preceding embodiment: wherein the first sensor is located at a different location on the subject than the second sensor; and wherein various spatial resolution of sensors enables detection of waveform differences between the different locations.

17. The method of any preceding embodiment, wherein detecting one or more events comprises acquiring spatial and temporal information regarding acoustic event source and propagation.

18. The method of any preceding embodiment, further comprising a second acoustic sensor located at a location of the neck of the subject where signal sources associated with blood flow and blood pressure change at the carotid artery may be detected.

19. The method of any preceding embodiment, wherein the data obtained from the second acoustic sensor is combined with the first acoustic sensor data.

20. The method of any preceding embodiment: wherein the first sensor comprises a cardiac acoustic sensor located at a location external to the subject and associated with the subject's heart; and wherein the method further comprises acquiring a third signal from a third sensor comprising a respiratory acoustic sensor located at a location associated with the patient's lung.

21. The method of any preceding embodiment, further comprising acquiring real-time measurement of one or more of thoracic motion and thoracic volume and lung mechanical response from a third sensor.

22. The method of any preceding embodiment: wherein the acoustic sensor is one of an array of acoustic sensors integrated into the wearable sensor unit, each said acoustic sensor having an associated vibration source integrated into the wearable sensor unit; and wherein the method further comprises periodically activating the vibration source associated with a sensor and determining if a different sensor detects a vibration signal from the vibration source.

23. The method of any preceding embodiment, further comprising acquiring real-time measurement of one or more of diaphragmatic motion and diaphragmatic volume and lung mechanical response from a third sensor.

24. The method of any preceding embodiment: wherein detecting one or more events comprises segmenting an acoustic signal of the acoustic sensor into frames; and wherein each frame corresponds to a time interval associated with one cardiac cycle.

25. The method of any preceding embodiment, wherein the frames are segmented so that each frame begins and ends relative to successive R-wave peaks.

26. The method of any preceding embodiment, further comprising identifying peaks in the acoustic signal as event candidates.

27. The method of any preceding embodiment, further comprising: classifying event candidates as one of a plurality of heart sound types.

28. The method of any preceding embodiment, further comprising: p extracting acoustic event features as a function of time and frequency domain features of acoustic events for each heartbeat.

29. The method of any preceding embodiment, further comprising: inputting the extracted acoustic event features into a regression model to output a desired physiological measurement to be predicted.

30. The method of any preceding embodiment, further comprising: inputting the extracted acoustic event features into a plurality of classification model models trained on previously obtained data; and wherein each model represents all possible scenarios in which the signal integrity from one or more, but not all, sensors is compromised.

31. A cardio-respiratory diagnostic apparatus, comprising: (a) a wearable sensor unit configured to be positioned external to a subject; (b) at least one acoustic sensor integrated into a wearable sensor unit; (c a computer processor; and (d) a memory storing instructions executable on the processor, the instructions, when executed by the processor, performing steps comprising: (i) acquiring data from the acoustic sensor; (ii) comparing data acquired from the acoustic sensor with data in a conditional probability table; and (iii) determining one or more cardio or respiratory conditions of the subject based on said comparison.

32. The apparatus of any preceding embodiment, further comprising: a first motion sensor for detection of thoracic expansion and contraction located at an upper abdominal location; and a second motion sensor for detection of diaphragmatic expansion and contraction located at a lower abdominal location.

33. The apparatus of any preceding embodiment, wherein when executed by the processor the instructions further perform steps comprising detecting signatures in time frequency domain characteristic of cardio or respiratory conditions of the subject.

34. The apparatus of any preceding embodiment, further comprising: at least a second acoustic sensor integrated into the wearable sensor unit; each said acoustic sensor having an associated vibration source integrated into the wearable sensor unit; said instructions when executed by the processor further performing steps comprising periodically activating the vibration source associated with a sensor and determine if a different sensor detects a vibration signal from the vibration source.

35. The apparatus of any preceding embodiment, wherein said instructions when executed by the processor performing steps comprising acquiring passive measurements of abdominal vibration and acoustic signals.

36. The apparatus of any preceding embodiment, said instructions when executed by the processor further performing steps comprising: synchronously acquiring acoustic data from a first sensor and physiological data from a second sensor; detecting one or more events in an acoustic signal acquired from the first sensor as a function of acquired physiological data from the second sensor; and determining one or more cardio or respiratory conditions of the patient based on the one or more detected events.

37. The apparatus of any preceding embodiment, wherein the second sensor comprises an electrocardiogram (ECG) for monitoring an ECG signal of the patient.

38. The apparatus of any preceding embodiment: wherein the first sensor comprises a cardiac acoustic sensor located at a location external to the patient associated with the subject's heart; and wherein the apparatus further comprises a third sensor comprising a respiratory acoustic sensor located at a location associated with the patient's lung.

39. The apparatus of any preceding embodiment, further comprising a third sensor configured for real-time measurement of one or more of thoracic motion and thoracic volume and lung mechanical response.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

|  | Sensor 1 | Sensor 2 | Sensor 3 | Sensor 4 |
| --- | --- | --- | --- | --- |
| Model 1 | + | − | − | − |
| Model 2 | − | + | − | − |
| Model 3 | − | − | + | − |
| Model 4 | − | − | − | + |
| Model 5 | + | + | − | − |
| Model 6 | + | − | + | − |
| Model 7 | + | − | − | + |
| Model 8 | − | + | + | − |
| Model 9 | − | + | − | + |
| Model 10 | − | − | + | + |
| Model 11 | + | + | + | − |
| Model 12 | + | + | − | + |
| Model 13 | + | − | + | + |
| Model 14 | − | + | + | + |
| Model 15 | + | + | + | + |

What is claimed is:

1. A multi-sensor cardio-respiratory system, comprising:
   (a) a first set of acoustic sensors configured to be disposed at a location external to a subject and configured to measure acoustic signals emanating from the subject, the subject having a known cardiac condition;
   (b) a second set of sensors configured to be disposed at a second location external to the subject, the second set of sensors configured to measure additional signals emanating from the subject;
   (c) a computer processor configured to acquire signals from the first and second set of sensors and transform the acquired signals into diagnostic signals representing one or more cardiac conditions of the subject, and output the diagnostic signals to an output device for identifying the one or more cardiac conditions of the subject; and
   (d) a memory storing instructions executable on the computer processor, the instructions, when executed by the computer processor, performing steps comprising:
      (i) synchronously acquiring data from the first set of acoustic sensors and the second set of sensors;
      (ii) detecting one or more events, time of events and frequency-domain characteristics in acoustic signals acquired from each sensor in the first set of acoustic sensors in relation to one or more events, time of events and frequency-domain characteristics in acquired data from each sensor in the second set of sensors;
      (iii) extracting a plurality of features from the acoustic signals as a function of the one or more detected events, time of events and frequency-domain characteristics from the first set of acoustic sensors and second set of sensors;
      (iv) inputting the plurality of features along with the subject's known cardiac condition to train a linear regression model for determining the one or more cardiac conditions; and
      (v) determining the one or more cardiac conditions of the subject based on operations on combined data from the trained linear regression model and one or more detected events, time of events and frequency-domain characteristics acquired from the subject; and
      (vi) wherein the one or more cardiac conditions comprises a value of ejection fraction or stroke volume of the subject.

2. A system as recited in claim 1:
   wherein the first set of acoustic sensors is located at a different location on the subject than the second set of sensors; and
   wherein operations on the time and frequency domain characteristics of signals from a combination of sensors within the first set of acoustic sensors and second set of sensors enables detection of signal waveform differences between the different locations for determining the one or more cardiac conditions.

3. A system as recited in claim 1, wherein detecting one or more events, time of events and frequency-domain characteristics comprises acquiring spatial information and identification of differences between each sensor within the first set of acoustic sensors and second set of sensors for time of occurrence and frequency-domain characteristics of each segment of emission waveforms in measured signals from first set and second set of sensors.

4. A system as recited in claim 1, wherein the second set of sensors comprises a plurality of electrocardiogram (ECG) sensors for monitoring time and frequency domain characteristics of an ECG signal of the subject.

5. A system as recited in claim 4:
   wherein the first set of acoustic sensors are located at a body surface location associated with a heart of the subject; and
   wherein the system further comprises a third set of sensors comprising respiratory acoustic sensor located at a body surface location associated with a lung of the subject for detection of signals emanating from a heart of the subject as generated by respiratory processes.

6. A system as recited in claim 4, further comprising a third set of sensors configured for real-time measurement of one or more of thoracic motion and thoracic volume and lung mechanical response.

7. A system as recited in claim 2:
   wherein the first set of acoustic sensors comprises an array of acoustic sensors integrated into a wearable sensor unit;
   each acoustic sensor within the first set of acoustic sensors having an associated vibration source integrated into the wearable sensor unit;
   said instructions when executed by the computer processor performing steps comprising periodically activating an associated vibration source associated with a sensor within the first set of acoustic sensors and determine if a different sensor within the first set of acoustic sensors detects a vibration signal from the associated vibration source.

8. A system as recited in claim 3:
wherein detecting one or more events comprises segmenting an acoustic signal of an acoustic sensor within the first set of acoustic sensors into frames within which specific events may appear; and
wherein each frame corresponds to a time interval comprising at least a segment of one cardiac cycle.

9. A system as recited in claim 8, wherein the frames are segmented so that each frame begins and ends relative to successive R-wave signal features.

10. A system as recited in claim 9, wherein when executed by the computer processor the instructions further perform steps comprising identifying peaks in the acoustic signal as event candidates.

11. A system as recited in claim 10, wherein when executed by the computer processor the instructions further perform steps comprising classifying event candidates as one of a plurality of heart sound types.

12. A system as recited in claim 1, wherein the trained linear regression model comprises a regression model trained from the input plurality of features extracted from an acoustic event.

13. A system as recited in 7, further comprising:
a first motion sensor coupled to the wearable sensor unit for detection of thoracic expansion and contraction located at an upper abdominal location; and
a second motion sensor coupled to the wearable sensor unit for detection of diaphragmatic expansion and contraction located at a lower abdominal location.

14. A system as recited in claim 1, wherein the trained linear regression model comprises a conditional probability table trained from the extracted plurality of features such that data acquired from the subject may be compared with data in the conditional probability table to determine the one or more cardiac conditions of the subject.

* * * * *